United States Patent [19]

Osa et al.

[11] Patent Number: 5,300,251

[45] Date of Patent: Apr. 5, 1994

[54] CLATHRATE COMPOUNDS

[75] Inventors: Tetsuo Osa; Akihiko Ueno, both of Sendai; Atsushi Osakada, Nagoya; Masateru Nakoji, Okazaki, all of Japan

[73] Assignee: A-ICS Corporation, Aichi, Japan

[21] Appl. No.: 68,607

[22] Filed: May 27, 1993

Related U.S. Application Data

[63] Continuation of Ser. No. 562,589, Aug. 3, 1990, abandoned.

[30] Foreign Application Priority Data

Aug. 4, 1989 [JP] Japan .................. 1-201219

[51] Int. Cl.$^5$ .............................. C09K 3/00
[52] U.S. Cl. .................. 252/182.13; 252/182.12; 252/186.26; 536/103
[58] Field of Search ............. 252/186.26, 186.42, 252/182.13, 182.12; 536/103; 428/402.24

[56] References Cited

U.S. PATENT DOCUMENTS

| | | | |
|---|---|---|---|
| 4,746,734 | 5/1988 | Tsuchiyama et al. | 536/103 |
| 4,869,904 | 9/1989 | Uekama et al. | 536/103 |
| 5,008,386 | 4/1991 | Szabó et al. | 536/103 |

FOREIGN PATENT DOCUMENTS 63-295693 12/1988 Japan .................. 536/103

OTHER PUBLICATIONS

CA 73:76606e "Formation of Inclusion Compounds of B-Cyclobextrin With Hydroperoxides", by Matusi et al., Matue, Japan.

CA 73:76607F "Stabilization of Hydroporoxides by Means of the Formation of Inclusion Compounds With B-Cyclodextrin.", Matusi et al., Matue, Japan.

CA:99:38873u "Free Medical Polymerization of Water-Soluble Vinyl Monomers in Two-Phase (water/organic) System Using Methilated B-Cyclodextrins as Initiator Carriers.", Taguchi et al., Osaka, Japan.

Bender, M. L. and Komiyama, N. "Cyclodextrin Chemistry", Reactivity and Structure Concepts in Organic Chemistry, 6, Germany: Springer-Verlag Berlin Heidelberg, 1978, pp. 46–49.

European Search Report, Application No. EP 90308551.2, dated Nov. 15, 1990.

Chemical Abstract No. 76 607f, vol. 73, No. 15 (1970), p. 314.

Chemical Abstract No. 38 873u, vol. 99, No. 6 (Aug. 1983), p. 4.

Chemical Abstract No. 76 606e, vol. 73, No. 15 (1970), p. 314.

*Primary Examiner*—Richard D. Lovering
*Assistant Examiner*—Joseph D. Anthony
*Attorney, Agent, or Firm*—Cushman, Darby & Cushman

[57] ABSTRACT

Disclosed is a clathrate compound comprising an organic peroxide as a guest compound and at least one of natural and derived cyclodextrins as a host compound.

2 Claims, No Drawings

CLATHRATE COMPOUNDS

This is a continuation of application Ser. No. 07/562,589, filed on Aug. 3, 1990, which was abandoned upon the filing hereof.

BACKGROUND OF THE INVENTION (1) Field of the Invention

The present invention relates to a clathrate compound comprising an organic peroxide as a guest compound and at least one of natural and derived cyclodextrins as a host compound.

(2) Description of the Prior Art

Organic peroxides such as dicumyl peroxide, tert-butylcumyl peroxide, benzoyl peroxide and the like have widely been used as a crosslinking agent, free-radical reaction initiator, catalyst, curing agent, drying promotor, etc.

However, the organic peroxide is chemically unstable and incapable of being safely kept for a long period of time, and may cause explosion on receiving an impact, resulting in producing problems in its handling. The above organic peroxides are decomposed at very high speeds at high temperatures that a temperature range, in which effects are expectable, was limited.

On the other hand, it is known that cyclodextrin has a doughnut-like stereostructure, into a hollow space of which are taken in various guest compounds by clathration, or from the hollow space of which are taken out the various guest compounds.

Clathration between cyclodextrin as the host compound and known guest compounds generally provides various effects such as stabilization of volatile matter, antioxidating, deodorizing, relief from bitterness in bitter substances, emulsification of hardly soluble substances, etc.

Further, uses of the known clathrate compounds comprising cyclodextrin as the host compound and known guest compounds cover various fields such as foods, medicines, agricultural chemicals, cosmetics, toiletries, plastics, and the like.

For example, M. L. Bender and M. Kimiyama, Cyclodextrin Chemistry, Springer-Verlay, Berlin, 1978, discloses clathrate compounds comprising cyclodextrin as the host compound and a guest compound such as diphenyl carbonate, diphenyl pyrophosphate, methylphosphonic acid diphenyl ester or the like, and further discloses that the above guest compounds are very stable in a neutral and alkaline solution, but formation of clathrate compounds therefrom remarkably accelerates hydrolysis thereof.

However, no clathrate compounds comprising organic peroxide as the guest compound and cyclodextrin as the host compound are known.

SUMMARY OF THE INVENTION

It is an object of the present invention to provide novel clathrate compounds use of which results in making it possible to decompose the organic peroxide as the guest compound at higher temperatures and lower decomposition speed compared with the organic peroxide itself, and to improve properties of the organic peroxide as the guest compound in thermal stability, storage stability, photostability, impact resistance and solubility in water compared with the organic peroxide itself, resulting in making easy the handling of the organic peroxides used in the present invention and in increasing the application of the organic peroxides used in the present invention.

That is, the present invention provides a clathrate compound comprising an organic peroxide as a guest compound and at least one of natural and derived cyclodextrins (hereinafter may simply be referred to as cyclodextrin) as a host compound.

DETAILED DESCRIPTION OF THE INVENTION

The organic peroxide of the present invention may include any organic compounds having peroxide group in the molecule. Examples of the organic peroxide may include dicumyl peroxide, tert-butylcumyl peroxide, 2,5-dimethyl-2,5-di(tert-butylperoxy) hexane, 2,5-dimethyl-2,5-di(tert-butylperoxy) hexyne-3, 1,3-bis(tert-butylperoxyisopropyl)benzene, 1,1-bis-tert-butylperoxy-3,3,5-trimethyl cyclohexane, benzoyl peroxide and the like, dicumyl peroxide being particularly preferred.

The natural cyclodextrin of the present invention is prepared by acting an enzyme on a starch, and is a doughnut-like non-reduced oligo-saccharide in which glucose is linked in a cyclic form through α-1,4-linkage. The natural cyclodextrins containing 6 to 8 of the glucose moiety are preferred because of having a hollow hole inner diameter suitable for taking in the above organic peroxides as the guest compounds by clathration.

The α-cyclodextrin containing 6 of the glucose moiety, β-cyclodextrin containing 7 thereof and γ-cyclodextrin containing 8 thereof have a hollow hole inner diameter of 4.5 Å, 7.0 Å, 8.5 Å, respectively and all have a hollow hole depth of 7.0 Å.

The derived cyclodextrin in the present invention may include ones derived from the natural cyclodextrin by subjecting the natural cyclodextrin to a chemical reaction, for example, monomethylation, dimethylation, trimethylation, or random methylation (hereinafter may be referred to as partial methylation).

Specific examples of the derived cyclodextrin may include ones obtained by subjecting one hydroxyl group at C-2, C-3 or C-6 of the glucose moiety of α-cyclodextrin, β-cyclodextrin or γ-cyclodextrin (hereinafter may be referred to as α-, β- or γ-cyclodextrin) to methylation (hereinafter may be referred to as monomethylated cyclodextrins); ones obtained by subjecting respective hydroxyl groups at C-2 and C-3 of the glucose moiety of α-, β- or γ-cyclodextrin to methylation (herein may be referred to as dimethylated cyclodextrins) ones obtained by subjecting respective hydroxyl groups at C-2, C-3 and C-6 of the glucose moiety of α-, β- or γ-cyclodextrin to methylation (hereinafter may be referred to as trimethylated cyclodextrins); and ones obtained by subjecting respective hydroxyl groups at C-2, C-3 and C-6 of the glucose moiety of α-, β- or γ-cyclodextrin to random methylation (hereinafter may be referred to as partially methylated cyclodextrins).

The derived cyclodextrin of the present invention may be prepared by reacting the natural cyclodextrin with barium oxide and dimethylsulfuric acid or methyl iodide.

The natural cyclodextrin and the derived cyclodextrin in the present invention may be used alone or in combination.

The clathrate compound comprising the organic peroxide as a guest compound and at least one of the natural and derived cyclodextrin as a host compound is such that the organic peroxide as the guest compound is taken in by clathration into the central area of the hollow hole of the host compound having the doughnut-like stereostructure. The ratio of an amount of the organic peroxide to that of the host compound may vary depending on the size and shape of the organic peroxide, but is generally in the range of from 1:0.5 to 1:2 as a molar ratio. For example, one molecule of an organic peroxide may be taken in two or more molecules of the host compound by clathration when the size of the organic peroxide is so large.

A suitable combination of the organic peroxide with the host compound may be determined depending on a relationship between a size of the organic peroxide and a hollow hole inner diameter of the host compound. For example, β-cyclodextrin is suitable for dicumyl peroxide as the organic peroxide.

The clathrate compound of the present invention may be prepared, for example, by adding a liquid or powdery organic peroxide to a heated aqueous host compound solution at 40° to 80° C., preferably 50° to 60° C., followed by thoroughly stirring for about 20 to 60 minutes, cooling down to room temperature, collecting precipitates thus formed by filtration, washing the resulting solids with water, washing with a small amount of an organic solvent which is capable of dissolving the free organic peroxide not subjected to clathration, and by drying under reduced pressure.

The clathrate compound of the present invention may also be prepared by directly thoroughly mixing the host compound and the organic peroxide. In this case the organic peroxide is thoroughly mixed for about 10 to 30 minutes with the host compound at room temperature when the organic peroxide is liquid at room temperature, or at a temperature which is the meting point of the organic peroxide or higher and at which the organic peroxide is not decomposed, preferably at a temperature higher than the melting point by 5° to 10° C. when the organic peroxide is solid at room temperature but is stable at and above the melting point of the organic peroxide to obtain powder containing a clathrate compound. The resulting powder is washed with water, followed by washing with a small amount of an organic solvent which is capable of dissolving the free starting organic peroxide not subjected to clathration, and drying under reduced pressure to obtain a clathrate compound.

The latter process may be preferred from the industrial point of view.

Uses of the clathrate compound of the present invention may substantially be the same as those of the organic peroxide as the guest compound in the clathrate compound of the present invention except that the clathrate compound may be used under wider and more severe conditions compared with the organic peroxide, and may include crosslinking agent, free-radical reaction initiator, catalyst, curing agent, drying promotor, etc.

According to the present invention, there are provided novel clathrate compounds, use of which results in making it possible to decompose the organic peroxide as the guest compound at higher temperatures and lower decomposition speed compared with the organic peroxide itself, and to improve properties of the organic peroxide as the guest compound in thermal stability, storage stability, photostability, impact resistance and solubility in water compared with the organic peroxide itself, resulting in making easy the handling of the organic peroxides used in the present invention and in increasing the application of the organic peroxides used in the present invention. In other words, the present invention provides such novel clathrate compounds that the clathrate compound has highly improved properties to be easily handled and provides wider uses compared with the organic peroxides themselves used in the present invention in that the use of the clathrate compound of the present invention makes possible such a reaction as to be impossible to start in water, makes easy temperature control during reaction, increases a reaction temperature range, and so forth.

The present invention is explained more in detail by the following Examples.

EXAMPLE 1

A beaker was charged with 1,00 g of dicumyl peroxide (marketed by Nippon Oil & Fats Co., Ltd. under a trademark of PERCUMYL-D, PURITY: 98% or higher) to be melted by heating at 50° C., and 4.20 g of β-cyclodextrin was added to be thoroughly mixed for carrying out clathration. The clathrate compound-containing mixture was washed first with water and then with ethyl ether in a suitable amount respectively to wash away the free β-cyclodextrin and dicumyl peroxide which were not subjected to clathration. The resulting solid was subjected to elemental analysis. The results of which are shown as follows.

| Determined: | C: 51.13%; | H: 6.70% |
|---|---|---|
| Calculated: | C: 51.28%; | H: 6.60% |
| | (Chemical formula: $C_{60}H_{92}O_{37}$)[1] | |

The above results show that a clathrate compound comprising one mole of dicumyl peroxide and one mole of β-cyclodextrin is formed.

EXAMPLES 2 AND 4-7 AND COMPARATIVE EXAMPLE 2

Procedures of Example 1 were repeated except that β-cyclodexgrin (Example 2), α-cyclodextrin (Example 3), dimethyl-β-cyclodextrin (Examples 4 and 5) and partially methylated β-cyclodextrin (Examples 6 and 7) were used in such amounts as shown in Table-1 respectively with the results of elemental analysis as shown in Table-2, which show that clathrate compounds comprising one mole of guest compound and one mole of host compound were formed in Examples 1, 2, 4 5 and Comparative Example 2 respectively. The partially methylated β-cyclodextrin (PMCD) used in Examples 6 and 7 as shown in Table-1 is one marketed by SAN-RAKU Incorporated as such that an average degree of methylation is 68-71%, a degree of methylation at C-2 of the glucose moiety is 58-62%, a degree of methylation at C-3 of the glucose moiety is 48-52% and that a degree of methylation at C-6 of the glucose moiety is 98-100%.

COMPARATIVE EXAMPLE 1

The same dicumyl peroxide as in Example 1 is used for comparison without using the host compounds as in Examples.

TABLE-1

| Examples & Comp. Ex. | Guest Compound | Host Compound | Molar ratio of guest compound:host compound | Amount (g) of guest compound | Amount (g) of host compound |
|---|---|---|---|---|---|
| Ex. 1 | dicumyl peroxide | $\beta$-cyclodextrin | 1:1 | 1.00 | 4.20 |
| Ex. 2 | " | $\beta$-cyclodextrin | 1:2 | 0.50 | 4.20 |
| Ex. 3 | " | $\gamma$-cyclodextrin | 1:1 | 1.00 | 4.80 |
| Ex. 4 | " | dimethyl-$\beta$-cyclodextrin | 1:1 | 1.00 | 4.92 |
| Ex. 5 | " | dimethyl-$\beta$-cyclodextrin | 1:2 | 0.50 | 4.92 |
| Ex. 6 | " | PMCD | 1:1 | 1.00 | 4.96 |
| Ex. 7 | " | PMCD | 1:2 | 0.50 | 4.96 |
| Comparative Ex. 1 | " | — | 1:0 | 1.00 | 0.00 |

TABLE-2

| Examples | Determined C% | Determined H% | Calculated C% | Calculated H% | Calculated Chemical formula |
|---|---|---|---|---|---|
| Ex. 2 | 51.25 | 7.02 | 51.28 | 6.60 | $C_{60}H_{92}O_{37}$ (2) |
| Comparative Ex. 2 | 50.02 | 6.78 | 49.99 | 6.61 | $C_{66}H_{102}O_{42}\cdot H_2O$ (3) |
| Ex. 4 | 55.12 | 7.72 | 55.00 | 7.38 | $C_{74}H_{116}O_{37}\cdot H_2O$ (3) |
| Ex. 5 | 54.98 | 7.41 | 55.00 | 7.38 | $C_{74}H_{116}O_{37}\cdot H_2O$ |

(1) A chemical formula of a clathrate compound having a molar ratio of 1:1 as dicumyl peroxide:$\beta$-cyclodextrin.
(2) A chemical formula of a monohydrate of a clathrate compound having a molar ratio of 1:1 as dicumyl peroxide:$\gamma$-cyclodextrin.
(3) A chemical formula of a monohydrate of a clathrate compound having a molar ratio of 1:1 as dicumyl peroxide:dimethyl-$\beta$-cyclodextrin.

Thermal stability tests of the dicumyl peroxide as the guest compound compared with the dicumyl peroxide itself were carried out as follows.

Separately, a test tube equipped with a stopper and having a diameter of 15 mm and a length of 100 mm was charged with 0.15 g of respective clathrate compound-containing mixtures obtained after the completion of mixing for clathration in 1, 2, 4–7 and Comparative Example 2, followed by sealing, leaving at rest in an oil bath (Riko MH-313 Type) at 125° C.±0.5° C. for a predetermined period of time as shown in Table-3, cooling with water, extracting with water and ethyl ether, separating the ethyl ether layer, distilling off the ethyl ether, and adding 0.5 ml of heavy chloroform for determining by nuclear magnetic resonance spectroscopy.

On the other hand, in Comparative Example 1, the same dicumyl peroxide as in Examples was subjected to the same heating test as in Examples 1, 2, 4–7 and Comparative Example 2, except that the step of cooling with water was followed directly by adding 0.5 ml of heavy chloroform for dissolving without extracting with water and ethyl ether and by determining nuclear magnetic resonance (NMR) spectrum.

Thermal stability of the dicumyl peroxide as the guest compound and as the dicumyl peroxide itself was evaluated by determining a degree of thermal decomposition by the above nuclear magnetic resonance (NMR) spectroscopy as explained below.

Dicumyl peroxide decomposes by heating according to the following equation:

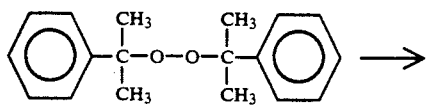

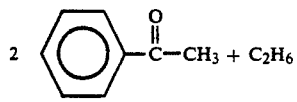

From the above equation, the following equation (I) is derived:

$$A_0 = A_t + 2B_t \qquad (I)$$

where $A_0$ is an initial value of an area of methyl proton in dicumyl peroxide on a NMR chart (at a time of t=0), $A_t$ is an area of methyl proton in dicumyl peroxide on a NMR chart at a time of t, and $B_t$ is an area of methyl proton in acetophenone on a NMR chart at a time of t.

The degree of thermal decomposition may be represented by the following equation (II):

$$\text{Degree of thermal decomposition (\%)} = \qquad (II)$$

$$\frac{(A_0 - A_t)}{A_0} \times 100\,(\%) = \frac{2B_t}{(A_t - 2B_t)} \times 100(\%)$$

Changes of the degree of thermal decomposition with time as the results of the above thermal stability tests are shown in Table-3.

TABLE-3

| Time (hr) | 0.5 | 1 | 1.5 | 2 | 3 | 4 | 5 |
|---|---|---|---|---|---|---|---|
| Example 1 | 8.9 | 14.2 | 16.5 | 24.2 | 27.4 | 32.9 | 37.5 |
| Example 2 | 6.25 | 8.2 | 15.8 | 21.8 | 26.4 | 31.6 | 36.5 |
| Comparative Example 2 | — | 17.2 | 20.2 | 26.8 | 26.3 | 32.8 | 38.1 |
| Example 4 | — | 9.5 | 9.5 | 12.2 | 24.0 | 23.6 | 27.5 |
| Example 5 | 0 | 0 | 5.1 | 6.7 | 15.4 | 27.7 | 24.8 |
| Example 6 | 0 | 4.2 | 27.1 | 44.3 | 53.2 | 63.2 | 67.8 |
| Example 7 | 0 | 3.8 | 21.2 | 40.3 | 52.3 | 61.1 | 64.5 |
| Comparative Example 1 | 16.7 | 26.5 | 32.9 | 41.9 | 48.9 | 50.7 | 53.3 |

The results shown in Table-3 show that decomposition speed of the dicumyl peroxide as the guest compound of the clathrate compounds formed in Examples 1, 2, 4, 5 and Comparative Example 2 is greatly reduced compared with that of the dicumyl peroxide itself as in Comparative Example 1, resulting in showing that thermal stability of the dicumyl peroxide as the guest compound of the clathrate compounds formed in Examples 1, 2, 4, 5 and Comparative Example 2 is remarkably improved compared with that of the dicumyl peroxide itself as in Comparative Example 1. The thermal stability of the dicumyl peroxide as the guest compound of the clathrate compound is the most improved in the case of the clathrate compound comprising dicumyl peroxide as the guest compound and dimethyl-$\beta$- cyclodextrin as the host compound as shown in Example 5.

The results of Examples 6 and 7 show that the use of partially methylated β-cyclodextrin as the host compound seems to accelerate the decomposition speed of dicumyl peroxide as the guest compound with time, but remarkably reduces the decomposition speed thereof for a certain period of time, for example, for about one hour from the beginning, resulting in showing remarkable thermal stability within a certain period of time, for example, about one hour under the conditions of Examples 6 and 7.

EXAMPLE 8

In 20 ml of water at 60° C. was dissolved 1 g of β-cyclodextrin, 0.25 g of dicumyl peroxide was added to the resulting solution to be a β-cyclodextrin: dicumyl peroxide molar ratio of 1:1, followed by stirring for 30 minutes in the state that the dicumyl peroxide is dispersed as oil drops. The resulting precipitates were collected on a glass filter to be washed with water, followed by washing with a small amount of ethyl ether under suction, and drying under reduced pressure to obtain a clathrate compound having a β-cyclodextrin: dicumyl peroxide molar ratio of 2:1.

The clathrate compound was subjected to elemental analysis with the following results:

| Calculated: | C: 48.22%; | H: 6.42% |
|---|---|---|
| | (Chemical formula: $C_{102}H_{162}O_{72}$) | |
| Determined | C: 48.16%; | H: 7.03% |

EXAMPLE 9

One gram of dicumyl peroxide was heated at 50° C. to be melted, and 0.5 g of β-cyclodextrin was added to be a β-cyclodextrin:dicumyl peroxide molar ratio of 1:8, followed by thoroughly mixing for clathration, washing the resulting product on a glass filter first with water and when with ethyl ether under suction, and drying under reduced pressure to obtain a clathrate compound having a β-cyclodextrin:dicumyl peroxide molar ratio of 1:1.

The clathrate compound was subjected to elemental analysis with the following results:

| Calculated: | C: 51.28%; | H: 6.60% |
|---|---|---|
| | (Chemical formula: $C_{60}H_{92}O_{37}$) | |
| Determined | C: 51.57%; | H: 7.06% |

What is claimed is:

1. A clathrate compound consisting of dicumyl peroxide as a guest compound and a host compound selected from the group consisting of β-cyclodextrin, monomethyl-β-cyclodextrin, dimethyl-β-cyclodextrin, trimethyl-β-cyclodextrin and partially methylated β-cyclodextrin, said dicumyl peroxide being used as a crosslinking agent, the molar ratio of the guest compound: the host compound being in the range of from 1:1 to 1:2 inclusive.

2. A clathrate compound as claimed in claim 1, wherein the molar ratio of the guest compound: the host compound is 1:2.

* * * * *